(12) United States Patent
Hölzemann et al.

(10) Patent No.: US 7,482,465 B2
(45) Date of Patent: Jan. 27, 2009

(54) INDOL DERIVATIVES AND THEIR USE AS 5-HT LIGANDS

(75) Inventors: Günter Hölzemann, Seeheim-Jugenheim (DE); Helene Crassier, Weiterstadt (DE); Henning Böttcher, Darmstadt (DE); Timo Heinrich, Gross-Umstadt (DE); Kai Schiemann, Darmstadt (DE); Joachim Leibrock, Pfungstadt (DE); Chrisoph Van Amsterdam, Darmstadt (DE); Gerd Bartoszyk, Weiterstadt (DE); Christoph Seyfried, Seeheim-Jugenheim (DE)

(73) Assignee: Merck Patent GmbH, Darmstadt (DE)

( * ) Notice: Subject to any disclaimer, the term of this patent is extended or adjusted under 35 U.S.C. 154(b) by 231 days.

(21) Appl. No.: 10/538,639

(22) PCT Filed: Nov. 17, 2003

(86) PCT No.: PCT/EP03/12810

§ 371 (c)(1),
(2), (4) Date: Jun. 10, 2005

(87) PCT Pub. No.: WO2004/052886

PCT Pub. Date: Jun. 24, 2004

(65) Prior Publication Data

US 2006/0116405 A1 Jun. 1, 2006

(30) Foreign Application Priority Data

Dec. 10, 2002 (EP) .................. 02027483

(51) Int. Cl.
*C07D 271/12* (2006.01)
*C07D 285/10* (2006.01)
(52) U.S. Cl. ...................... 548/126; 548/127
(58) Field of Classification Search ................ 548/126, 548/127

See application file for complete search history.

(56) References Cited

U.S. PATENT DOCUMENTS 5,002,948 A  3/1991  Perregaard et al.
6,150,533 A * 11/2000  Mewshaw et al. ........ 548/305.1

FOREIGN PATENT DOCUMENTS

EP           0 376 607        7/1990
WO         WO 00/49017        8/2000

OTHER PUBLICATIONS

Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the Internet, URL; http://www.cnn.com/2003/HEALTH/conditions/09/24/alzheimers.drug.ap/indexhtml>.*
Magnus, et al. Neural stem cells in inflammatory CNS diseases: mechanisms and therapy. J. Cell. Mol. Med.(2005) vol. 9, pp. 303-319.*
Schizophrenia Health Article [online], [retrieved on Aug. 16, 2007]. Retrieved from the Internet, URL; http://www.healthline.com/adamcontent/schizophrenia>.*
Medical Encyclopedia: Psychosis [online], [retrieved on Aug. 16, 2007]. Retrieved from the Internet, URL; http://www.nlm.nih.gov/medlineplus/print/enxy/article/001553.htm>.*
Vippagunta et al. Advanced Drug Delivery Reviews 48 (2001) 3-26.*

* cited by examiner

*Primary Examiner*—Kamal A Saeed
*Assistant Examiner*—Shawquia Young
(74) *Attorney, Agent, or Firm*—Millen, White, Zelano, & Branigan, P.C.

(57) ABSTRACT

The invention relates to indol derivatives of Formula (I) in which R1, R2, R3, X, A, n, m and p have the meanings indicated above.

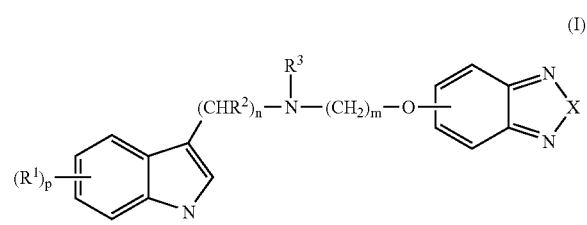

5 Claims, No Drawings

INDOL DERIVATIVES AND THEIR USE AS 5-HT LIGANDS

The invention relates to indol derivatives, their preparation and their use as pharmaceuticals.

The indol derivatives according to the invention can be represented by the general formula I

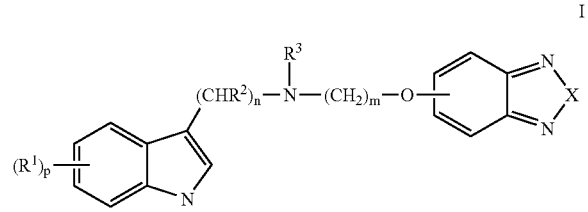

wherein
$R^1$ is H, OH, OA, CN Hal, COR, or $CH_2R$,
R is OH, OA, $NH_2$, NHA, or $NA_2$,
$R^2$ and $R^3$ are H or A,
A is an alkyl group with 1-10 atomes,
X is O or S,
Hal is F, Cl, Br or I
n is 2-6,
m is 1-4
p is 0, 1, 2, 3 or 4
and their salts and solvates, enantiomeres, racemates and other mixtures of enantiomeres.

The on hand invention is a selection invention, because other indol derivatives are known from WO 94/24127, WO 90/05721 or JP 05043544.

It is the object of the invention to make available medicaments, in particular psycho pharmaceuticals. It is a preferred object of the invention to make available compounds which bind specifically to a single type of 5-HT receptors such as $5\text{-}HT_{1A/1D/2A/2C}$.

The compounds in this invention also inhibits the serotonin reuptake, they are particular suitable as anti depressive and anxiolytic drugs. They also show serotonin agonistic and -antagonistic characteristics. The compounds compete with serotonin ligands binding hippocampuses receptors (Cossery et al., European J. Pharmacol. 140 (1987), 143-155) and inhibit the synaptosomal serotonin reuptake (Sherman et al., Life Sci. 23 (1978), 1863-1870). The ex vivo test system uses the inhibition of serotonin reuptake due to competition or synaptosomal reuptake (Wong et al., Neuropsychopharmacol. 8 (1993) and the p-chloramphetamine antagonism (Fuller et al., J. Pharmacol. Exp. Ther. 212 (1980), 115-119). The $5\text{-}HT_{1D}$-Affinity is detectable with a method from Pauwels and Palmier that is described in Neuropharmacology, 33, 67 (1994).

This object is achieved by the compounds of the general formula I and by their tolerable salts and solvates (see above).

It has been found that the compounds of the formula I and their salts have very valuable pharmacological properties together with good tolerability. They especially act as ligands of the 5-HT-receptor on the central nervous system. They have, in particular, a high affinity for receptors of the $5\text{-}HT_{1A}$ type.

Compounds of the formula I are particularly preferably simultaneously agonists of the 5-HT receptor. Compounds that bind to a single type of 5-HT receptor are preferred, e.g. compounds binding only to $5\text{-}HT_{1A}$ but not to $5\text{-}HT_{1D/2A/2C}$ or binding only to $5\text{-}HT_{1D}$ but not to $5\text{-}HT_{1A/2A/2C}$, or binding only to $5\text{-}HT_{2A}$ but not to $5\text{-}HT_{1A/1D/2C}$, or binding only to $5\text{-}HT_{2C}$ but not to $5\text{-}HT_{1A/1D/2A}$.

Binding properties of the compounds of the formula I can be determined by known $5\text{-}HT_{1A}$ (serotonin) binding test ($5\text{-}HT_{1A}$ (serotonin) binding test: Matzen et al., J. Med. Chem., 43, 1149-1157, (2000) in particular page 1156 with reference to Eur. J. Pharmacol.: 140, 143-155 (1987).

For the in-vitro detection of the affinity for $5\text{-}HT_{2A}$ receptors, it is possible to use, for example, the following test (Example A1). The $5\text{-}HT_{2A}$ receptors are exposed to both [$^3$H]ketanserin (a substance known for its affinity for the receptor) and the test compound. The decrease in the affinity of [$^3$H]ketanserin for the receptor is a sign of the affinity of the test substance for the $5\text{-}HT_{2A}$ receptor. Detection is carried out analogously to the description of J. E. Leysen et al., Molecular Pharmacology, 1982, 21: 301-314 or as also described, for example, in EP 0320983.

The efficacy of the compounds according to the invention as $5\text{-}HT_{2A}$ receptor antagonists can be measured in vitro analogously to W. Feniuk et al., Mechanisms of 5-hydroxytryptamine-induced vasoconstriction, in: The Peripheral Actions of 5-Hydroxytryptamine, ed. Fozard J R, Oxford University Press, New York, 1989, p. 110. Thus the contractility of the rat tail artery, caused by 5-hydroxytryptamine, is mediated by $5\text{-}HT_{2A}$ receptors. For the test system, vessel rings, prepared from the ventral rat tail artery, are subjected to perfusion with an oxygen-saturated solution in an organ bath. By introduction of increasing concentrations of 5-hydroxytryptamine into the solution, a response to the cumulative concentration of 5-HT is obtained. The test compound is then added to the organ bath in suitable concentrations and a second concentration curve is measured for 5-HT. The strength of the test compound on the shift of the 5-HT-induced concentration curve to higher 5-HT concentrations is a measure of the $5\text{-}HT_{2A}$ receptor-antagonistic property in vitro.

The $5\text{-}HT_{2A}$-antagonistic property can be determined in vivo analogously to M. D. Serdar et al., Psychopharmacology, 1996, 128: 198-205.

The compounds according to the invention can be employed for the control and treatment of diseases which are associated with the serotinin neurotransmitter system and in which high-affinity serotinin receptors ($5\text{-}HT_{1A}$ receptors) are involved. The most important indication for the administration of the compound of the general formula I are psychoses of any type, in particular also mental disorders of the schizophrenia type. Moreover, the compounds can also be employed for the reduction of cognitive functional disorders, i.e. for improvement of the learning ability and of the memory. The compounds of the general formula I are also suitable for the control of the symptoms of Alzheimer's disease. The substances of the general formula I according to the invention are moreover suitable for the prophylaxis and control of cerebral infarcts (cerebral apoplexy), such as cerebral stroke and cerebral ischaemia. The substances are also suitable for the treatment of disorders such as pathological anxiety states, overexcitation, hyperactivity and attention disorders in children and adolescents, deep-seated developmental disorders and disorders of social behavior with mental retardation, depression, compulsive disorders in the narrower (OCD) and wider sense (OCSD), certain sexual function disorders, sleep disorders and eating disorders, and also such psychiatric symptoms in the context of senile dementia and dementia of the Alzheimer type, i.e. diseases of the central nervous system in the widest sense.

The compounds of the general formula I and their tolerable salts and solvates can thus be employed as pharmaceutical active ingredients of medicaments such as anxiolytics, antidepressants, neuroleptics and/or antihypertensives.

A is preferably H or $C_1$-$C_6$-alkyl, where 1 to 7 hydrogen atoms are optionally replaced by fluorine. A can be branched or unbranched and is preferably methyl, ethyl, propyl, isopropyl, n-butyl, sec-butyl, tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethyl-buytyl, 1- or 2-ethylbutyl, 1-ethyl-1-methylpropyl, 1-ethyl-2-methylpropyl, 1,1,2- or 1,2,2-trimethylpropyl. Particularly preferably, A is methyl, ethyl, isopropyl, n-propyl, n-butyl or tert-butyl.

Compounds of the formula I are also particularly preferred in which $R^1$ and $R^2$ are simultaneously H, and compounds of the formula I in which $R^1$ has the meaning alkyl and $R^2$ has the meaning H.

The general formula I preferably has one of the following Meanings Ia to If:

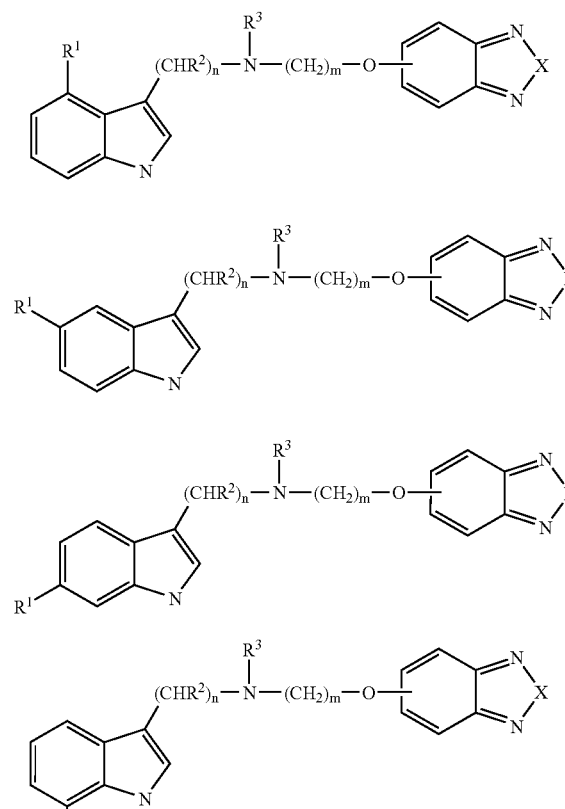

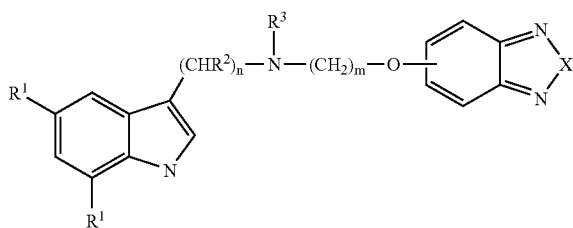

Wherein $R^1$, $R^2$, $R^3$, A, X, n and m have the meaning given above.

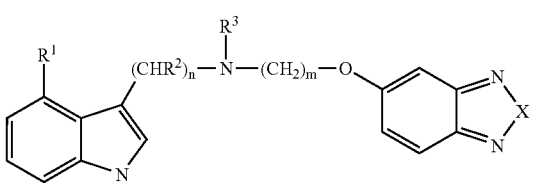

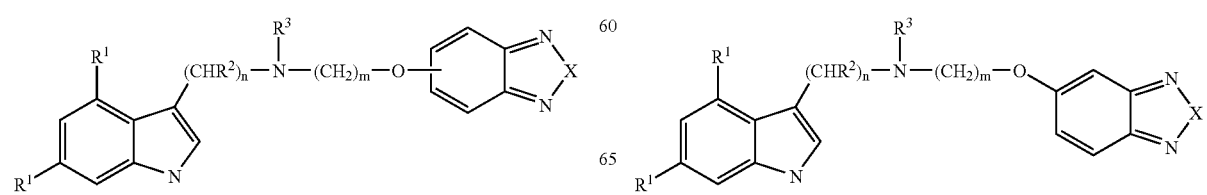

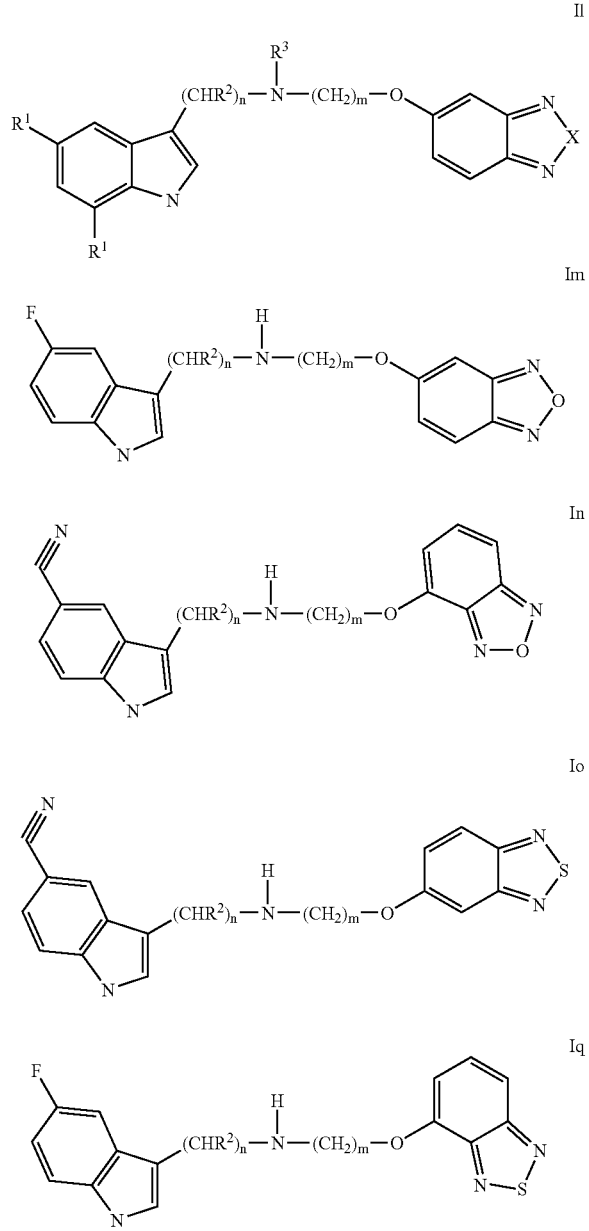
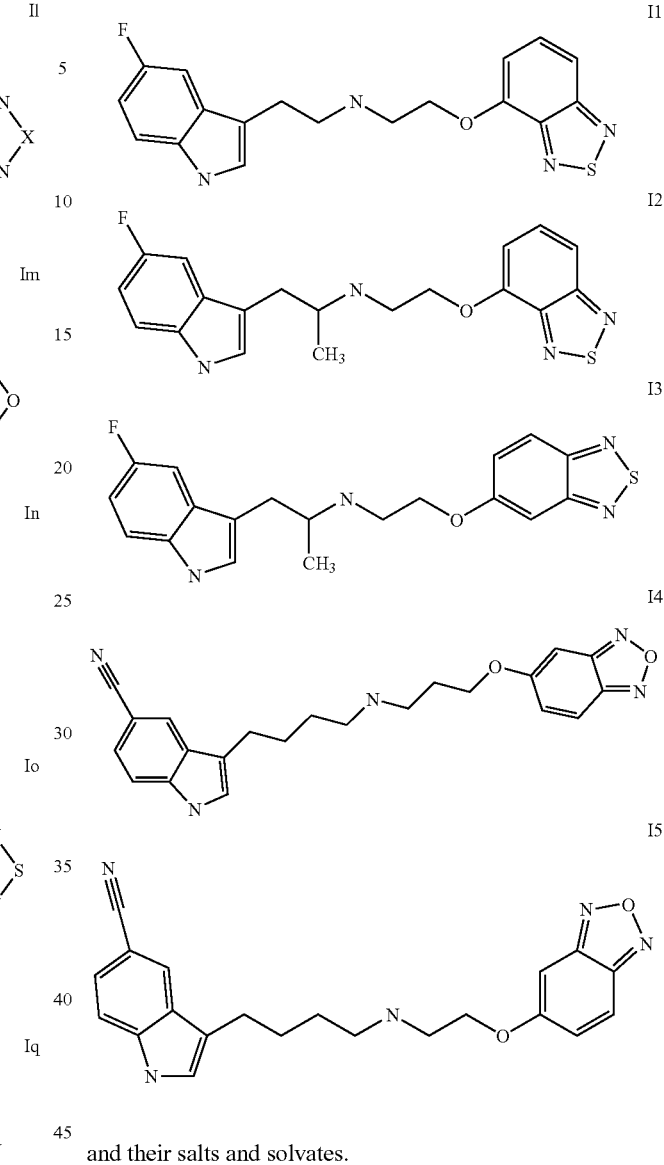

wherein

R¹, R² and R³ have the meaning given above.

Hal is F, Cl, Br or I, where F and Cl, in particular F, are preferred.

n is preferably 2, 3, 4, 5, 6, where n equals 3 is particularly preferred.

m is preferably 1, 2, 3, or 4 and especially 2.

The substituents R¹, R², and A can independently of one another assume one of the abovementioned meanings. The compounds of the general formula I are thus all the more strongly preferred, the more of their substituents have preferred meanings and the greater these meanings are preferred.

Compounds selected from the following group of the compounds Ia to Iq and I1 to I5 are particularly preferred:

and their salts and solvates.

If the compounds of the general formula I are optically active, the formula I includes both any isolated optical antipodes and the corresponding optionally racemic mixtures in any conceivable composition.

A compound of the general formula I can be converted into the corresponding salt (that is acid addition salt) using an acid. Acids which afford the tolerable (that is biocompatible and adequately bioavailable) salts are suitable for this reaction. It is thus possible to use inorganic acids such as sulfuric acid or hydrohalic acids such as hydrochloric acid, bromic acid or phosphoric acids such as orthophosphoric acid, nitric acid, sulfamic acid, aliphatic, alicyclic, araliphatic, aromatic or heterocyclic monobasic or polybasic carboxylic acids, sulfonic acids or sulfuric acid derivatives such as formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2-phenylpropionic acid, citric acid, gluconic acid, ascorbic acid, nicotinic acid, isonicotinic acid, methanesulfonic acid or ethanesulfonic acid, ethanedisulfonic acid, 2-hydroxyethanesulfonic acid, benzenesulfonic acid, paratoluenesulfonic acid, naphthalenemonosulfonic acid and naphthalenedisulfonic acid and sulfuric acid lauryl ester in order to obtain the corresponding acid addition salt.

If desired, the corresponding free bases of the general formula I can be liberated by the treatment of their salts with strong bases such as sodium hydroxide, potassium hydroxide or sodium or potassium carbonate, provided that no other acidic groups are present in the molecule. In the last-mentioned cases, in which the compounds of the general formula I carry free acidic groups, salt formation can also be brought about by treatment with strong bases. Suitable bases are alkali metal hydroxides, alkaline earth metal hydroxides, or organic bases in the form of primary, secondary or tertiary amines.

Solvates of the compounds of the general formula I are understood as meaning adducts of chemically "inert" solvent molecules to the compounds of the formula I which are formed on account of their mutual attractive force. Solvates are, for example, mono- and dihydrates or addition compounds with alcohols such as methanol or ethanol.

It is known that pharmaceuticals can be converted synthetically into derivatives (for example into alkyl or acryl derivatives, into sugar or oligopeptide derivatives and others) which are converted back into the active compounds of the general formula I in the body metabolically by extra cellular or intracellular enzymes. The invention also relates to such "prodrug derivatives" of the compounds of the general formula I.

A further subject of the invention is the use of a compound of the general formula I or of one of its tolerable salts or solvates for the production of a medicament which is suitable for the treatment and or control of human or animal disorders, in particular of disorders of the central nervous system such as pathological stress states, depression and/or psychoses, for the reduction of side effects during the treatment of high blood pressure (e.g. with α-methyldopa), for the treatment of endocrinological and/or gynaecological disorders, e.g. for the treatment of acromegaly, hypogonadism, secondary amenorrhoea, the post-menstrual syndrome and undesired lactation in puberty and for the prophylaxis and therapy of cerebral disorders (e.g. of migraine), in particular in geriatrics, in a similar manner to specific ergot alkaloids and for the control and prophylaxis of cerebral infarct (cerebral apoplexy) such as cerebral stroke and cerebral ischaemia. Moreover, the pharmaceutical preparations and medicaments which contain a compound of the general formula I are suitable for improvement of the cognitive functional ability and for the treatment of Alzheimer's disease symptoms. In particular, such medicaments are suitable for the treatment of mental disorders of the schizophrenia type and for the control of psychotic anxiety states. The term treatment in the context of the invention includes prophylaxis and therapy of human or animal diseases.

The substances of the general formula I are normally administered analogously to known, commercially obtainable pharmaceutical preparations (e.g. of bromocriptine and dihydroergocornine), preferably in doses of between 0.2 mg and 500 mg, in particular of between 0.2 and 15 mg per dose unit. The daily dose unit is between 0.001 and 10 mg per kg of body weight. Low doses (of between 0.2 and 1 mg per dose unit, 0.001 to 0.005 mg per kg of body weight) are particularly suitable for pharmaceutical preparations for the treatment of migraine. A dose of between 10 and 50 mg per dose unit is preferred for other indications. However, the dose to be administered depends on a large number of factors, e.g. on the efficacy of the corresponding component, the age, the body weight and the general condition of the patient.

The invention relates to the compounds of the formula I according to Claim 1 and their physiologically acceptable salts or solvates as pharmaceutical active compounds and/or pharmaceutical preparations containing at least one compound of the formula I.

The invention also relates to the compounds of the formula I according to Claim 1 and their physiologically acceptable salts or solvates for the production of a medicament. These medicament is useful for the treatment of illnesses which can be influenced by the binding of the compound of formula I according to Claim 1 and their physiologically acceptable salts or solvates to the 5-HT receptors.

The invention furthermore relates to compounds of the formula I according to Claim 1 and their physiologically acceptable salts or solvates as $5HT_{1A}$ agonists and serotonin reuptake inhibitor.

The invention also relates to the compounds of the formula I according to Claim 1 and their physiologically acceptable salts or solvates for use in the control of diseases.

A further subject of the invention is a process for the production of a pharmaceutical preparation, which comprises the conversion of a compound of the general formula I or of one of its tolerable salts or solvates to a suitable dose form together with a suitable vehicle. The compounds of the general formula I can be brought into a suitable dose form together with at least one vehicle or excipient, if appropriate in combination with a further active ingredient.

Furthermore the subject of the invention is the use of compounds according to Claim 1 and/or their physiologically acceptable salts or solvates, enantiomeres or recemates for the production of a medicament for the treatment of illnesses of the central nervous system, in particular of mental disorders of the schizophrenia type and for the control of psychotic anxiety states.

Suitable vehicles are organic or inorganic substances which are suitable for enteral (e.g. oral) or parenteral or topical administration and which do not react with the substances of the general formula I according to the invention. Examples of such vehicles are water, vegetable oils, benzyl alcohols, polyethylene glycols, gelatin, carbohydrates such as lactose and starch, magnesium stearate, talc and raw petroleum jelly. Tablets, coated tablets, capsules, syrups, juices, drops or suppositories are in particular employed for enteral administration. Solutions, preferably oily or aqueous solutions, such as suspensions, emulsions or alternatively implants are used for parenteral administration. Ointments, creams or powders are employed in the case of external application. The compounds of the general formula I can also be lyophilized and the resulting lyophilizates processed to give injectable preparations.

The invention further relates to medicaments which contain at least one compound of the general formula I or one of its tolerable salts or solvates and, if appropriate, further ingredients such as vehicles, excipients etc. These preparations can be employed as medicaments for the treatment of human or animal diseases.

The aforementioned medicaments can be sterilized and processed together with excipients such as lubricants, preservatives, stabilizers and/or wetting agents, emulsifiers, osmotically active substances, buffers, colorants or flavor enhancers to give other pharmaceutical preparations.

The compounds of the formula I and also the starting substances for their preparation are otherwise prepared by methods known per se, such as are described in the literature (e.g. in the standard works such as Houben-Weyl, Methoden der organischen Chemie [Methods of organic chemistry], Georg-Thieme-Verlag, Stuttgart), namely under reaction conditions which are known and suitable for the reactions mentioned. Use can also be made in this case of variants which are known per se, but not mentioned here in greater detail.

If desired, the starting substances can also be formed in situ such that they are not isolated from the reaction mixture, but immediately reacted further to give the compounds of the formula I.

The indol derivatives of the formula I are preferably prepared according to the following scheme:

Scheme 1:

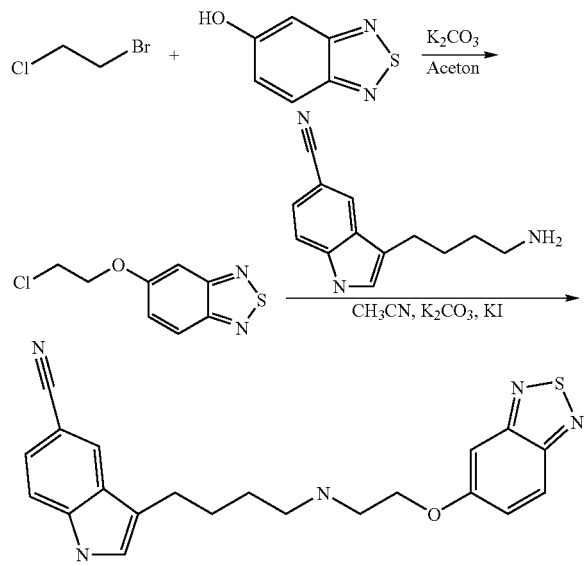

The invention is described by the following examples:

The molecular weight (M+H⁺) is determined with the aid of electron spray ionization mass spectroscopy. The mass-spectroscopic data derive from HPLC/MSC runs (HPLC coupled with an electrospray ionization mass spectrometer). The numerical values are, as customary in this procedure, not the molecular weights of the unmodified compounds, but the molecular weights of the protonated compounds (below: [M+H⁺]). The method is described in the following references: M. Yamashita, J. B. Fenn, J. Phys. Chem. 88, 1984, 4451-4459; C. K. Meng et al., Zeitschrift für Physik D 10, 1988, 361-368; J. B. Fenn et al., Science 246, 1989, 64-71.

EXAMPLE A a) 2.5 g $K_2CO_3$ and 10 mg KI were added to a mixture of 2.7 g benzo [1.2.3] thiadiazol-5-ol and 6.0 ml 1-bromo-3-chlorethan in 30 ml acetone. The resulting mixture was heated for 4 days under reflux. The solvent was removed and the residue subjected to conventional work up, which result in yellow crystals of 5-(2-chloro-ethoxy)-benzol[1.2.3]thiadiazole ([M+H]⁺: 215).

b) 386 mg $K_2CO_3$ and 166 mg KI were added to a mixture of 200 mg 5-(2-chloro-ethoxy)-benzol[1.2.3]thiadiazole and 233 mg 3.4-amino-butyl)-1H-indole-5-carbonitrile in 10 ml acetonitrile. The resulting mixture was heated for three days under reflux.

The reaction mixture was poured in water/ice bath and subjected to conventional work up.

The purification of the product is achieving by preparative HPLC:

| Column: | RP 18 (15 µm) Lichrosorb 250 × 50 |
|---|---|
| solvent: | A: 98 $H_2O$, 2 $CH_3CN$, 0.1% TFA |
|  | B: 10 $H_2O$, 90 $CH_3CN$, 0.1% TFA |
| UV: | 225 nm; one range |
| Flow rate: | 10 ml/min |

The purification resulted in bright yellow crystals of 3-{4-[2-(benzo[1,2,5]thiadiazol-4-yloxy)-ethylamino]-butyl}-1H-indole-5-carbonitrile as TFA salt ($R_f$ in $H_2O$/methanol 1/1=0.27; ([M+H]⁺: 392).

EXAMPLE B a) 3.9 g $K_2CO_3$ and 50 mg KI were added to the mixture of 1.0 g 2.1.3-benzoxodiazol-5-ol and 2.5 ml 1-bromo-2-chlorethan in 50 ml acetonitrile. The resulting mixture was boiled over night under reflux. After removal of the solvent the residue is subjected to conventional work up, which results in yellow crystals of 5-(2-chloro-ethoxy)-benzol[1.2.3]oxadiazole ([M+H]⁺: 199).

b) A mixture of 760 mg $K_2CO_3$ and 30 mg KI were added to 430 mg 5-(2-chloro-ethoxy)-benzol[1.2.3] oxadiazole and 400 mg 5-fluortryptamine in 30 ml acetonitrile. The resulting mixture was boiled for 4 days under reflux. After removal of the solvent the residue is subjected to conventional work up, which results in a bright solid substance of the 3-{2-[2-(benzo[1,2,5]oxadiazol-5-yloxy)-ethylamino]-ethyl}-1H-indol-5-carbonitrile ([M+H]⁺: 341).

EXAMPLES 1-144

Ia1

| No. | R¹ | n | m | x |
|---|---|---|---|---|
| 1. | OH | 2 | 1 | O |
| 2. | OH | 3 | 1 | O |
| 3. | OH | 4 | 1 | O |
| 4. | OH | 2 | 2 | O |
| 5. | OH | 3 | 2 | O |
| 6. | OH | 4 | 2 | O |
| 7. | OH | 2 | 3 | O |
| 8. | OH | 3 | 3 | O |
| 9. | OH | 4 | 3 | O |
| 10. | OH | 2 | 4 | O |
| 11. | OH | 3 | 4 | O |
| 12. | OH | 4 | 4 | O |
| 13. | OMe | 2 | 1 | O |
| 14. | OMe | 3 | 1 | O |
| 15. | OMe | 4 | 1 | O |
| 16. | OMe | 2 | 2 | O |
| 17. | OMe | 3 | 2 | O |
| 18. | OMe | 4 | 2 | O |
| 19. | OMe | 2 | 3 | O |
| 20. | OMe | 3 | 3 | O |
| 21. | OMe | 4 | 3 | O |
| 22. | OMe | 2 | 4 | O |
| 23. | OMe | 3 | 4 | O |
| 24. | OMe | 4 | 4 | O |
| 25. | CN | 2 | 1 | O |

-continued

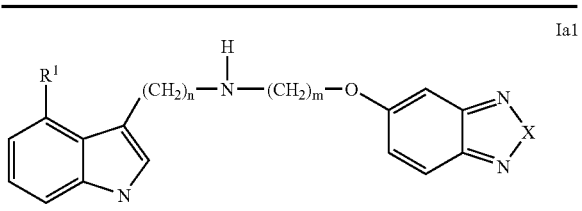

Ia1

| No. | R¹ | n | m | x |
|---|---|---|---|---|
| 26. | CN | 3 | 1 | O |
| 27. | CN | 4 | 1 | O |
| 28. | CN | 2 | 2 | O |
| 29. | CN | 3 | 2 | O |
| 30. | CN | 4 | 2 | O |
| 31. | CN | 2 | 3 | O |
| 32. | CN | 3 | 3 | O |
| 33. | CN | 4 | 3 | O |
| 34. | CN | 2 | 4 | O |
| 35. | CN | 3 | 4 | O |
| 36. | CN | 4 | 4 | O |
| 37. | F | 2 | 1 | O |
| 38. | F | 3 | 1 | O |
| 39. | F | 4 | 1 | O |
| 40. | F | 2 | 2 | O |
| 41. | F | 3 | 2 | O |
| 42. | F | 4 | 2 | O |
| 43. | F | 2 | 3 | O |
| 44. | F | 3 | 3 | O |
| 45. | F | 4 | 3 | O |
| 46. | F | 2 | 4 | O |
| 47. | F | 3 | 4 | O |
| 48. | F | 4 | 4 | O |
| 49. | Cl | 2 | 1 | O |
| 50. | Cl | 3 | 1 | O |
| 51. | Cl | 4 | 1 | O |
| 52. | Cl | 2 | 2 | O |
| 53. | Cl | 3 | 2 | O |
| 54. | Cl | 4 | 2 | O |
| 55. | Cl | 2 | 3 | O |
| 56. | Cl | 3 | 3 | O |
| 57. | Cl | 4 | 3 | O |
| 58. | Cl | 2 | 4 | O |
| 59. | Cl | 3 | 4 | O |
| 60. | Cl | 4 | 4 | O |
| 61. | $OC_2H_5$ | 2 | 1 | O |
| 62. | $OC_2H_5$ | 3 | 1 | O |
| 63. | $OC_2H_5$ | 4 | 1 | O |
| 64. | $OC_2H_5$ | 2 | 2 | O |
| 65. | $OC_2H_5$ | 3 | 2 | O |
| 66. | $OC_2H_5$ | 4 | 2 | O |
| 67. | $OC_2H_5$ | 2 | 3 | O |
| 68. | $OC_2H_5$ | 3 | 3 | O |
| 69. | $OC_2H_5$ | 4 | 3 | O |
| 70. | $OC_2H_5$ | 2 | 4 | O |
| 71. | $OC_2H_5$ | 3 | 4 | O |
| 72. | $OC_2H_5$ | 4 | 4 | O |
| 73. | OH | 2 | 1 | O |
| 74. | OH | 3 | 1 | O |
| 75. | OH | 4 | 1 | O |
| 76. | OH | 2 | 2 | O |
| 77. | OH | 3 | 2 | O |
| 78. | OH | 4 | 2 | O |
| 79. | OH | 2 | 3 | O |
| 80. | OH | 3 | 3 | O |
| 81. | OH | 4 | 3 | O |
| 82. | OH | 2 | 4 | O |
| 83. | OH | 3 | 4 | O |
| 84. | OH | 4 | 4 | O |
| 85. | OMe | 2 | 1 | O |
| 86. | OMe | 3 | 1 | O |
| 87. | OMe | 4 | 1 | O |
| 88. | OMe | 2 | 2 | O |
| 89. | OMe | 3 | 2 | O |
| 90. | OMe | 4 | 2 | O |
| 91. | OMe | 2 | 3 | O |
| 92. | OMe | 3 | 3 | O |

-continued

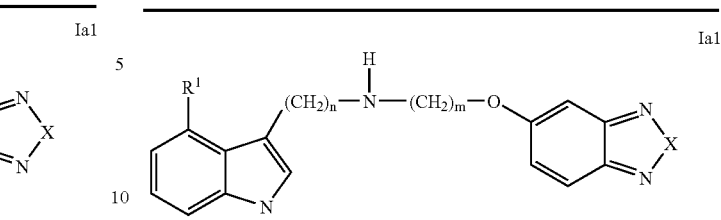

Ia1

| No. | R¹ | n | m | x |
|---|---|---|---|---|
| 93. | OMe | 4 | 3 | O |
| 94. | OMe | 2 | 4 | O |
| 95. | OMe | 3 | 4 | O |
| 96. | OMe | 4 | 4 | O |
| 97. | CN | 2 | 1 | O |
| 98. | CN | 3 | 1 | O |
| 99. | CN | 4 | 1 | O |
| 100. | CN | 2 | 2 | O |
| 101. | CN | 3 | 2 | O |
| 102. | CN | 4 | 2 | S |
| 103. | CN | 2 | 3 | S |
| 104. | CN | 3 | 3 | S |
| 105. | CN | 4 | 3 | S |
| 106. | CN | 2 | 4 | S |
| 107. | CN | 3 | 4 | S |
| 108. | CN | 4 | 4 | S |
| 109. | F | 2 | 1 | S |
| 110. | F | 3 | 1 | S |
| 111. | F | 4 | 1 | S |
| 112. | F | 2 | 2 | S |
| 113. | F | 3 | 2 | S |
| 114. | F | 4 | 2 | S |
| 115. | F | 2 | 3 | S |
| 116. | F | 3 | 3 | S |
| 117. | F | 4 | 3 | S |
| 118. | F | 2 | 4 | S |
| 119. | F | 3 | 4 | S |
| 120. | F | 4 | 4 | S |
| 121. | Cl | 2 | 1 | S |
| 122. | Cl | 3 | 1 | S |
| 123. | Cl | 4 | 1 | S |
| 124. | Cl | 2 | 2 | S |
| 125. | Cl | 3 | 2 | O |
| 126. | Cl | 4 | 2 | S |
| 127. | Cl | 2 | 3 | S |
| 128. | Cl | 3 | 3 | S |
| 129. | Cl | 4 | 3 | S |
| 130. | Cl | 2 | 4 | S |
| 131. | Cl | 3 | 4 | S |
| 132. | Cl | 4 | 4 | S |
| 133. | $OC_2H_5$ | 2 | 1 | S |
| 134. | $OC_2H_5$ | 3 | 1 | S |
| 135. | $OC_2H_5$ | 4 | 1 | S |
| 136. | $OC_2H_5$ | 2 | 2 | S |
| 137. | $OC_2H_5$ | 3 | 2 | S |
| 138. | $OC_2H_5$ | 4 | 2 | S |
| 139. | $OC_2H_5$ | 2 | 3 | S |
| 140. | $OC_2H_5$ | 3 | 3 | S |
| 141. | $OC_2H_5$ | 4 | 3 | S |
| 142. | $OC_2H_5$ | 2 | 4 | S |
| 143. | $OC_2H_5$ | 3 | 4 | S |
| 144. | $OC_2H_5$ | 4 | 4 | S |

EXAMPLES 145-288

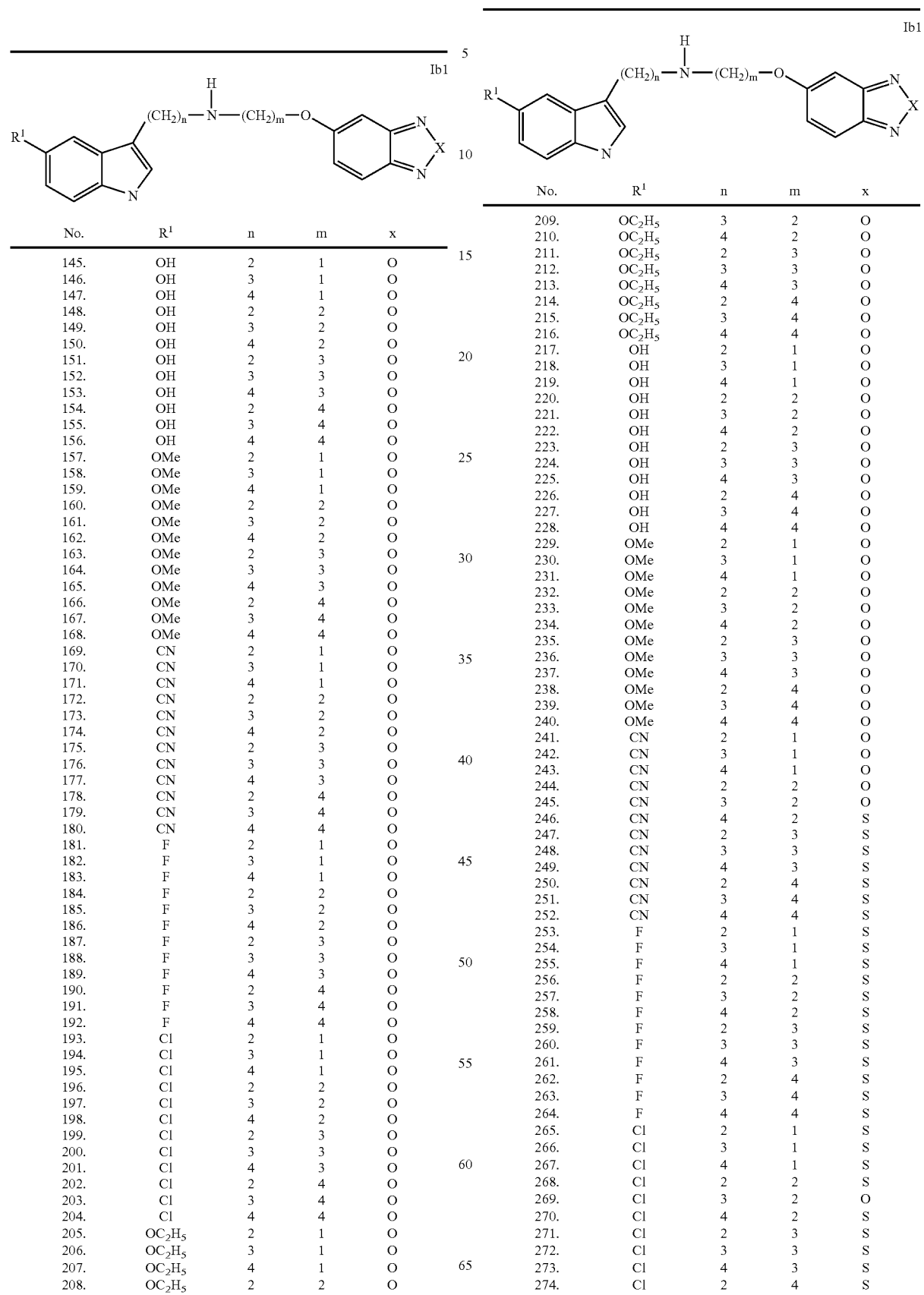

| No. | R¹ | n | m | x |
|---|---|---|---|---|
| 145. | OH | 2 | 1 | O |
| 146. | OH | 3 | 1 | O |
| 147. | OH | 4 | 1 | O |
| 148. | OH | 2 | 2 | O |
| 149. | OH | 3 | 2 | O |
| 150. | OH | 4 | 2 | O |
| 151. | OH | 2 | 3 | O |
| 152. | OH | 3 | 3 | O |
| 153. | OH | 4 | 3 | O |
| 154. | OH | 2 | 4 | O |
| 155. | OH | 3 | 4 | O |
| 156. | OH | 4 | 4 | O |
| 157. | OMe | 2 | 1 | O |
| 158. | OMe | 3 | 1 | O |
| 159. | OMe | 4 | 1 | O |
| 160. | OMe | 2 | 2 | O |
| 161. | OMe | 3 | 2 | O |
| 162. | OMe | 4 | 2 | O |
| 163. | OMe | 2 | 3 | O |
| 164. | OMe | 3 | 3 | O |
| 165. | OMe | 4 | 3 | O |
| 166. | OMe | 2 | 4 | O |
| 167. | OMe | 3 | 4 | O |
| 168. | OMe | 4 | 4 | O |
| 169. | CN | 2 | 1 | O |
| 170. | CN | 3 | 1 | O |
| 171. | CN | 4 | 1 | O |
| 172. | CN | 2 | 2 | O |
| 173. | CN | 3 | 2 | O |
| 174. | CN | 4 | 2 | O |
| 175. | CN | 2 | 3 | O |
| 176. | CN | 3 | 3 | O |
| 177. | CN | 4 | 3 | O |
| 178. | CN | 2 | 4 | O |
| 179. | CN | 3 | 4 | O |
| 180. | CN | 4 | 4 | O |
| 181. | F | 2 | 1 | O |
| 182. | F | 3 | 1 | O |
| 183. | F | 4 | 1 | O |
| 184. | F | 2 | 2 | O |
| 185. | F | 3 | 2 | O |
| 186. | F | 4 | 2 | O |
| 187. | F | 2 | 3 | O |
| 188. | F | 3 | 3 | O |
| 189. | F | 4 | 3 | O |
| 190. | F | 2 | 4 | O |
| 191. | F | 3 | 4 | O |
| 192. | F | 4 | 4 | O |
| 193. | Cl | 2 | 1 | O |
| 194. | Cl | 3 | 1 | O |
| 195. | Cl | 4 | 1 | O |
| 196. | Cl | 2 | 2 | O |
| 197. | Cl | 3 | 2 | O |
| 198. | Cl | 4 | 2 | O |
| 199. | Cl | 2 | 3 | O |
| 200. | Cl | 3 | 3 | O |
| 201. | Cl | 4 | 3 | O |
| 202. | Cl | 2 | 4 | O |
| 203. | Cl | 3 | 4 | O |
| 204. | Cl | 4 | 4 | O |
| 205. | OC$_2$H$_5$ | 2 | 1 | O |
| 206. | OC$_2$H$_5$ | 3 | 1 | O |
| 207. | OC$_2$H$_5$ | 4 | 1 | O |
| 208. | OC$_2$H$_5$ | 2 | 2 | O |
| 209. | OC$_2$H$_5$ | 3 | 2 | O |
| 210. | OC$_2$H$_5$ | 4 | 2 | O |
| 211. | OC$_2$H$_5$ | 2 | 3 | O |
| 212. | OC$_2$H$_5$ | 3 | 3 | O |
| 213. | OC$_2$H$_5$ | 4 | 3 | O |
| 214. | OC$_2$H$_5$ | 2 | 4 | O |
| 215. | OC$_2$H$_5$ | 3 | 4 | O |
| 216. | OC$_2$H$_5$ | 4 | 4 | O |
| 217. | OH | 2 | 1 | O |
| 218. | OH | 3 | 1 | O |
| 219. | OH | 4 | 1 | O |
| 220. | OH | 2 | 2 | O |
| 221. | OH | 3 | 2 | O |
| 222. | OH | 4 | 2 | O |
| 223. | OH | 2 | 3 | O |
| 224. | OH | 3 | 3 | O |
| 225. | OH | 4 | 3 | O |
| 226. | OH | 2 | 4 | O |
| 227. | OH | 3 | 4 | O |
| 228. | OH | 4 | 4 | O |
| 229. | OMe | 2 | 1 | O |
| 230. | OMe | 3 | 1 | O |
| 231. | OMe | 4 | 1 | O |
| 232. | OMe | 2 | 2 | O |
| 233. | OMe | 3 | 2 | O |
| 234. | OMe | 4 | 2 | O |
| 235. | OMe | 2 | 3 | O |
| 236. | OMe | 3 | 3 | O |
| 237. | OMe | 4 | 3 | O |
| 238. | OMe | 2 | 4 | O |
| 239. | OMe | 3 | 4 | O |
| 240. | OMe | 4 | 4 | O |
| 241. | CN | 2 | 1 | O |
| 242. | CN | 3 | 1 | O |
| 243. | CN | 4 | 1 | O |
| 244. | CN | 2 | 2 | O |
| 245. | CN | 3 | 2 | O |
| 246. | CN | 4 | 2 | S |
| 247. | CN | 2 | 3 | S |
| 248. | CN | 3 | 3 | S |
| 249. | CN | 4 | 3 | S |
| 250. | CN | 2 | 4 | S |
| 251. | CN | 3 | 4 | S |
| 252. | CN | 4 | 4 | S |
| 253. | F | 2 | 1 | S |
| 254. | F | 3 | 1 | S |
| 255. | F | 4 | 1 | S |
| 256. | F | 2 | 2 | S |
| 257. | F | 3 | 2 | S |
| 258. | F | 4 | 2 | S |
| 259. | F | 2 | 3 | S |
| 260. | F | 3 | 3 | S |
| 261. | F | 4 | 3 | S |
| 262. | F | 2 | 4 | S |
| 263. | F | 3 | 4 | S |
| 264. | F | 4 | 4 | S |
| 265. | Cl | 2 | 1 | S |
| 266. | Cl | 3 | 1 | S |
| 267. | Cl | 4 | 1 | S |
| 268. | Cl | 2 | 2 | S |
| 269. | Cl | 3 | 2 | O |
| 270. | Cl | 4 | 2 | S |
| 271. | Cl | 2 | 3 | S |
| 272. | Cl | 3 | 3 | S |
| 273. | Cl | 4 | 3 | S |
| 274. | Cl | 2 | 4 | S |

-continued

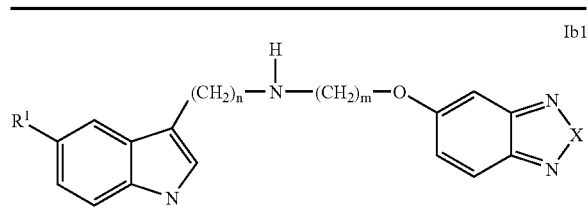

Ib1

| No. | R¹ | n | m | x |
|---|---|---|---|---|
| 275. | Cl | 3 | 4 | S |
| 276. | Cl | 4 | 4 | S |
| 277. | OC₂H₅ | 2 | 1 | S |
| 278. | OC₂H₅ | 3 | 1 | S |
| 279. | OC₂H₅ | 4 | 1 | S |
| 280. | OC₂H₅ | 2 | 2 | S |
| 281. | OC₂H₅ | 3 | 2 | S |
| 282. | OC₂H₅ | 4 | 2 | S |
| 283. | OC₂H₅ | 2 | 3 | S |
| 284. | OC₂H₅ | 3 | 3 | S |
| 285. | OC₂H₅ | 4 | 3 | S |
| 286. | OC₂H₅ | 2 | 4 | S |
| 287. | OC₂H₅ | 3 | 4 | S |
| 288. | OC₂H₅ | 4 | 4 | S |

EXAMPLES 289-432

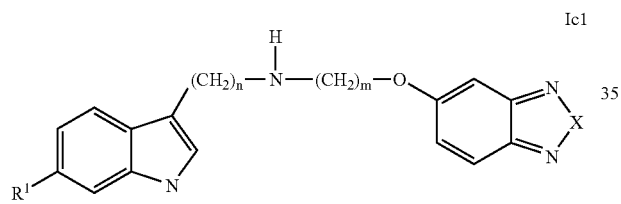

Ic1

| No. | R¹ | n | m | x |
|---|---|---|---|---|
| 289. | OH | 2 | 1 | O |
| 290. | OH | 3 | 1 | O |
| 291. | OH | 4 | 1 | O |
| 292. | OH | 2 | 2 | O |
| 293. | OH | 3 | 2 | O |
| 294. | OH | 4 | 2 | O |
| 295. | OH | 2 | 3 | O |
| 296. | OH | 3 | 3 | O |
| 297. | OH | 4 | 3 | O |
| 298. | OH | 2 | 4 | O |
| 299. | OH | 3 | 4 | O |
| 300. | OH | 4 | 4 | O |
| 301. | OMe | 2 | 1 | O |
| 302. | OMe | 3 | 1 | O |
| 303. | OMe | 4 | 1 | O |
| 304. | OMe | 2 | 2 | O |
| 305. | OMe | 3 | 2 | O |
| 306. | OMe | 4 | 2 | O |
| 307. | OMe | 2 | 3 | O |
| 308. | OMe | 3 | 3 | O |
| 309. | OMe | 4 | 3 | O |
| 310. | OMe | 2 | 4 | O |
| 311. | OMe | 3 | 4 | O |
| 312. | OMe | 4 | 4 | O |
| 313. | CN | 2 | 1 | O |
| 314. | CN | 3 | 1 | O |
| 315. | CN | 4 | 1 | O |
| 316. | CN | 2 | 2 | O |
| 317. | CN | 3 | 2 | O |
| 318. | CN | 4 | 2 | O |
| 319. | CN | 2 | 3 | O |

-continued

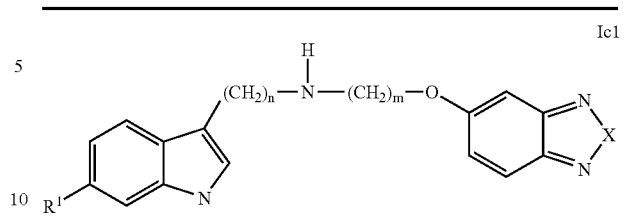

Ic1

| No. | R¹ | n | m | x |
|---|---|---|---|---|
| 320. | CN | 3 | 3 | O |
| 321. | CN | 4 | 3 | O |
| 322. | CN | 2 | 4 | O |
| 323. | CN | 3 | 4 | O |
| 324. | CN | 4 | 4 | O |
| 325. | F | 2 | 1 | O |
| 326. | F | 3 | 1 | O |
| 327. | F | 4 | 1 | O |
| 328. | F | 2 | 2 | O |
| 329. | F | 3 | 2 | O |
| 330. | F | 4 | 2 | O |
| 331. | F | 2 | 3 | O |
| 332. | F | 3 | 3 | O |
| 333. | F | 4 | 3 | O |
| 334. | F | 2 | 4 | O |
| 335. | F | 3 | 4 | O |
| 336. | F | 4 | 4 | O |
| 337. | Cl | 2 | 1 | O |
| 338. | Cl | 3 | 1 | O |
| 339. | Cl | 4 | 1 | O |
| 340. | Cl | 2 | 2 | O |
| 341. | Cl | 3 | 2 | O |
| 342. | Cl | 4 | 2 | O |
| 343. | Cl | 2 | 3 | O |
| 344. | Cl | 3 | 3 | O |
| 345. | Cl | 4 | 3 | O |
| 346. | Cl | 2 | 4 | O |
| 347. | Cl | 3 | 4 | O |
| 348. | Cl | 4 | 4 | O |
| 349. | OC₂H₅ | 2 | 1 | O |
| 350. | OC₂H₅ | 3 | 1 | O |
| 351. | OC₂H₅ | 4 | 1 | O |
| 352. | OC₂H₅ | 2 | 2 | O |
| 353. | OC₂H₅ | 3 | 2 | O |
| 354. | OC₂H₅ | 4 | 2 | O |
| 355. | OC₂H₅ | 2 | 3 | O |
| 356. | OC₂H₅ | 3 | 3 | O |
| 357. | OC₂H₅ | 4 | 3 | O |
| 358. | OC₂H₅ | 2 | 4 | O |
| 359. | OC₂H₅ | 3 | 4 | O |
| 360. | OC₂H₅ | 4 | 4 | O |
| 361. | OH | 2 | 1 | O |
| 362. | OH | 3 | 1 | O |
| 363. | OH | 4 | 1 | O |
| 364. | OH | 2 | 2 | O |
| 365. | OH | 3 | 2 | O |
| 366. | OH | 4 | 2 | O |
| 367. | OH | 2 | 3 | O |
| 368. | OH | 3 | 3 | O |
| 369. | OH | 4 | 3 | O |
| 370. | OH | 2 | 4 | O |
| 371. | OH | 3 | 4 | O |
| 372. | OH | 4 | 4 | O |
| 373. | OMe | 2 | 1 | O |
| 374. | OMe | 3 | 1 | O |
| 375. | OMe | 4 | 1 | O |
| 376. | OMe | 2 | 2 | O |
| 377. | OMe | 3 | 2 | O |
| 378. | OMe | 4 | 2 | O |
| 379. | OMe | 2 | 3 | O |
| 380. | OMe | 3 | 3 | O |
| 381. | OMe | 4 | 3 | O |
| 382. | OMe | 2 | 4 | O |
| 383. | OMe | 3 | 4 | O |

-continued

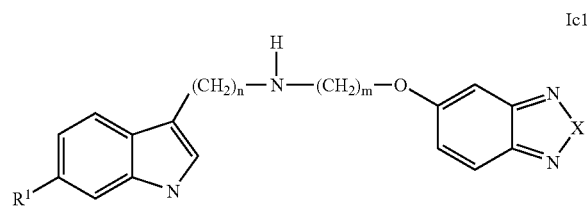

Ic1

| No. | R¹ | n | m | x |
|---|---|---|---|---|
| 384. | OMe | 4 | 4 | O |
| 385. | CN | 2 | 1 | O |
| 386. | CN | 3 | 1 | O |
| 387. | CN | 4 | 1 | O |
| 388. | CN | 2 | 2 | O |
| 389. | CN | 3 | 2 | O |
| 390. | CN | 4 | 2 | S |
| 391. | CN | 2 | 3 | S |
| 392. | CN | 3 | 3 | S |
| 393. | CN | 4 | 3 | S |
| 394. | CN | 2 | 4 | S |
| 395. | CN | 3 | 4 | S |
| 396. | CN | 4 | 4 | S |
| 397. | F | 2 | 1 | S |
| 398. | F | 3 | 1 | S |
| 399. | F | 4 | 1 | S |
| 400. | F | 2 | 2 | S |
| 401. | F | 3 | 2 | S |
| 402. | F | 4 | 2 | S |
| 403. | F | 2 | 3 | S |
| 404. | F | 3 | 3 | S |
| 405. | F | 4 | 3 | S |
| 406. | F | 2 | 4 | S |
| 407. | F | 3 | 4 | S |
| 408. | F | 4 | 4 | S |
| 409. | Cl | 2 | 1 | S |
| 410. | Cl | 3 | 1 | S |
| 411. | Cl | 4 | 1 | S |
| 412. | Cl | 2 | 2 | S |
| 413. | Cl | 3 | 2 | O |
| 414. | Cl | 4 | 2 | S |
| 415. | Cl | 2 | 3 | S |
| 416. | Cl | 3 | 3 | S |
| 417. | Cl | 4 | 3 | S |
| 418. | Cl | 2 | 4 | S |
| 419. | Cl | 3 | 4 | S |
| 420. | Cl | 4 | 4 | S |
| 421. | OC₂H₅ | 2 | 1 | S |
| 422. | OC₂H₅ | 3 | 1 | S |
| 423. | OC₂H₅ | 4 | 1 | S |
| 424. | OC₂H₅ | 2 | 2 | S |
| 425. | OC₂H₅ | 3 | 2 | S |
| 426. | OC₂H₅ | 4 | 2 | S |
| 427. | OC₂H₅ | 2 | 3 | S |
| 428. | OC₂H₅ | 3 | 3 | S |
| 429. | OC₂H₅ | 4 | 3 | S |
| 430. | OC₂H₅ | 2 | 4 | S |
| 431. | OC₂H₅ | 3 | 4 | S |
| 432. | OC₂H₅ | 4 | 4 | S |

EXAMPLES 433–576

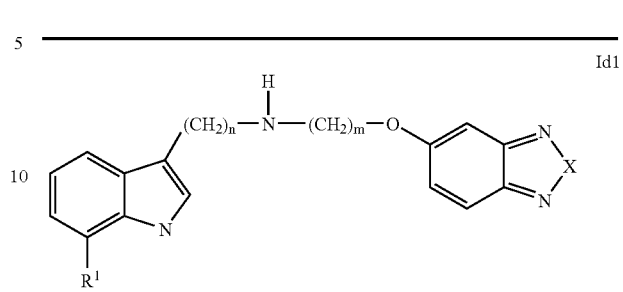

Id1

| No. | R¹ | n | m | x |
|---|---|---|---|---|
| 433. | OH | 2 | 1 | O |
| 434. | OH | 3 | 1 | O |
| 435. | OH | 4 | 1 | O |
| 436. | OH | 2 | 2 | O |
| 437. | OH | 3 | 2 | O |
| 438. | OH | 4 | 2 | O |
| 439. | OH | 2 | 3 | O |
| 440. | OH | 3 | 3 | O |
| 441. | OH | 4 | 3 | O |
| 442. | OH | 2 | 4 | O |
| 443. | OH | 3 | 4 | O |
| 444. | OH | 4 | 4 | O |
| 445. | OMe | 2 | 1 | O |
| 446. | OMe | 3 | 1 | O |
| 447. | OMe | 4 | 1 | O |
| 448. | OMe | 2 | 2 | O |
| 449. | OMe | 3 | 2 | O |
| 450. | OMe | 4 | 2 | O |
| 451. | OMe | 2 | 3 | O |
| 452. | OMe | 3 | 3 | O |
| 453. | OMe | 4 | 3 | O |
| 454. | OMe | 2 | 4 | O |
| 455. | OMe | 3 | 4 | O |
| 456. | OMe | 4 | 4 | O |
| 457. | CN | 2 | 1 | O |
| 458. | CN | 3 | 1 | O |
| 459. | CN | 4 | 1 | O |
| 460. | CN | 2 | 2 | O |
| 461. | CN | 3 | 2 | O |
| 462. | CN | 4 | 2 | O |
| 463. | CN | 2 | 3 | O |
| 464. | CN | 3 | 3 | O |
| 465. | CN | 4 | 3 | O |
| 466. | CN | 2 | 4 | O |
| 467. | CN | 3 | 4 | O |
| 468. | CN | 4 | 4 | O |
| 469. | F | 2 | 1 | O |
| 470. | F | 3 | 1 | O |
| 471. | F | 4 | 1 | O |
| 472. | F | 2 | 2 | O |
| 473. | F | 3 | 2 | O |
| 474. | F | 4 | 2 | O |
| 475. | F | 2 | 3 | O |
| 476. | F | 3 | 3 | O |
| 477. | F | 4 | 3 | O |
| 478. | F | 2 | 4 | O |
| 479. | F | 3 | 4 | O |
| 480. | F | 4 | 4 | O |
| 481. | Cl | 2 | 1 | O |
| 482. | Cl | 3 | 1 | O |
| 483. | Cl | 4 | 1 | O |
| 484. | Cl | 2 | 2 | O |
| 485. | Cl | 3 | 2 | O |
| 486. | Cl | 4 | 2 | O |
| 487. | Cl | 2 | 3 | O |
| 488. | Cl | 3 | 3 | O |
| 489. | Cl | 4 | 3 | O |
| 490. | Cl | 2 | 4 | O |
| 491. | Cl | 3 | 4 | O |
| 492. | Cl | 4 | 4 | O |
| 493. | OC₂H₅ | 2 | 1 | O |
| 494. | OC₂H₅ | 3 | 1 | O |

-continued

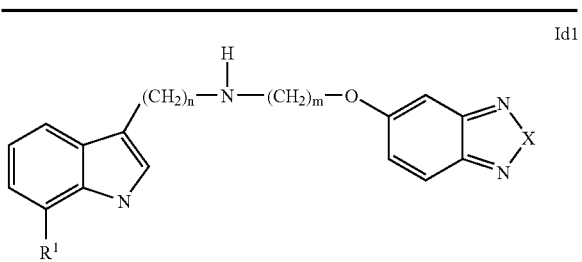

Id1

| No. | R¹ | n | m | x |
|---|---|---|---|---|
| 495. | OC₂H₅ | 4 | 1 | O |
| 496. | OC₂H₅ | 2 | 2 | O |
| 497. | OC₂H₅ | 3 | 2 | O |
| 498. | OC₂H₅ | 4 | 2 | O |
| 499. | OC₂H₅ | 2 | 3 | O |
| 500. | OC₂H₅ | 3 | 3 | O |
| 501. | OC₂H₅ | 4 | 3 | O |
| 502. | OC₂H₅ | 2 | 4 | O |
| 503. | OC₂H₅ | 3 | 4 | O |
| 504. | OC₂H₅ | 4 | 4 | O |
| 505. | OH | 2 | 1 | O |
| 506. | OH | 3 | 1 | O |
| 507. | OH | 4 | 1 | O |
| 508. | OH | 2 | 2 | O |
| 509. | OH | 3 | 2 | O |
| 510. | OH | 4 | 2 | O |
| 511. | OH | 2 | 3 | O |
| 512. | OH | 3 | 3 | O |
| 513. | OH | 4 | 3 | O |
| 514. | OH | 2 | 4 | O |
| 515. | OH | 3 | 4 | O |
| 516. | OH | 4 | 4 | O |
| 517. | OMe | 2 | 1 | O |
| 518. | OMe | 3 | 1 | O |
| 519. | OMe | 4 | 1 | O |
| 520. | OMe | 2 | 2 | O |
| 521. | OMe | 3 | 2 | O |
| 522. | OMe | 4 | 2 | O |
| 523. | OMe | 2 | 3 | O |
| 524. | OMe | 3 | 3 | O |
| 525. | OMe | 4 | 3 | O |
| 526. | OMe | 2 | 4 | O |
| 527. | OMe | 3 | 4 | O |
| 528. | OMe | 4 | 4 | O |
| 529. | CN | 2 | 1 | O |
| 530. | CN | 3 | 1 | O |
| 531. | CN | 4 | 1 | O |
| 532. | CN | 2 | 2 | O |
| 533. | CN | 3 | 2 | O |
| 534. | CN | 4 | 2 | S |
| 535. | CN | 2 | 3 | S |
| 536. | CN | 3 | 3 | S |
| 537. | CN | 4 | 3 | S |
| 538. | CN | 2 | 4 | S |
| 539. | CN | 3 | 4 | S |
| 540. | CN | 4 | 4 | S |
| 541. | F | 2 | 1 | S |
| 542. | F | 3 | 1 | S |
| 543. | F | 4 | 1 | S |
| 544. | F | 2 | 2 | S |
| 545. | F | 3 | 2 | S |
| 546. | F | 4 | 2 | S |
| 547. | F | 2 | 3 | S |
| 548. | F | 3 | 3 | S |
| 549. | F | 4 | 3 | S |
| 550. | F | 2 | 4 | S |
| 551. | F | 3 | 4 | S |
| 552. | F | 4 | 4 | S |
| 553. | Cl | 2 | 1 | S |
| 554. | Cl | 3 | 1 | S |
| 555. | Cl | 4 | 1 | S |
| 556. | Cl | 2 | 2 | S |
| 557. | Cl | 3 | 2 | O |
| 558. | Cl | 4 | 2 | S |

-continued

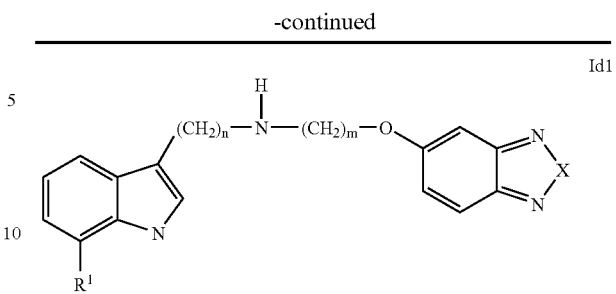

Id1

| No. | R¹ | n | m | x |
|---|---|---|---|---|
| 559. | Cl | 2 | 3 | S |
| 560. | Cl | 3 | 3 | S |
| 561. | Cl | 4 | 3 | S |
| 562. | Cl | 2 | 4 | S |
| 563. | Cl | 3 | 4 | S |
| 564. | Cl | 4 | 4 | S |
| 565. | OC₂H₅ | 2 | 1 | S |
| 566. | OC₂H₅ | 3 | 1 | S |
| 567. | OC₂H₅ | 4 | 1 | S |
| 568. | OC₂H₅ | 2 | 2 | S |
| 569. | OC₂H₅ | 3 | 2 | S |
| 570. | OC₂H₅ | 4 | 2 | S |
| 571. | OC₂H₅ | 2 | 3 | S |
| 572. | OC₂H₅ | 3 | 3 | S |
| 573. | OC₂H₅ | 4 | 3 | S |
| 574. | OC₂H₅ | 2 | 4 | S |
| 575. | OC₂H₅ | 3 | 4 | S |
| 576. | OC₂H₅ | 4 | 4 | S |

EXAMPLES 577-720

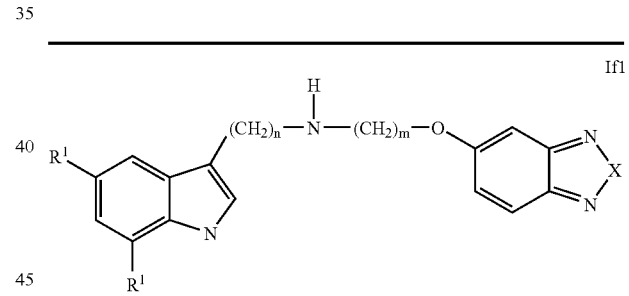

If1

| No. | R¹ | n | m | x |
|---|---|---|---|---|
| 577. | OH | 2 | 1 | O |
| 578. | OH | 3 | 1 | O |
| 579. | OH | 4 | 1 | O |
| 580. | OH | 2 | 2 | O |
| 581. | OH | 3 | 2 | O |
| 582. | OH | 4 | 2 | O |
| 583. | OH | 2 | 3 | O |
| 584. | OH | 3 | 3 | O |
| 585. | OH | 4 | 3 | O |
| 586. | OH | 2 | 4 | O |
| 587. | OH | 3 | 4 | O |
| 588. | OH | 4 | 4 | O |
| 589. | OMe | 2 | 1 | O |
| 590. | OMe | 3 | 1 | O |
| 591. | OMe | 4 | 1 | O |
| 592. | OMe | 2 | 2 | O |
| 593. | OMe | 3 | 2 | O |
| 594. | OMe | 4 | 2 | O |
| 595. | OMe | 2 | 3 | O |
| 596. | OMe | 3 | 3 | O |
| 597. | OMe | 4 | 3 | O |
| 598. | OMe | 2 | 4 | O |
| 599. | OMe | 3 | 4 | O |

-continued

If1

| No. | R¹ | n | m | x |
|-----|-----|---|---|---|
| 600. | OMe | 4 | 4 | O |
| 601. | CN | 2 | 1 | O |
| 602. | CN | 3 | 1 | O |
| 603. | CN | 4 | 1 | O |
| 604. | CN | 2 | 2 | O |
| 605. | CN | 3 | 2 | O |
| 606. | CN | 4 | 2 | O |
| 607. | CN | 2 | 3 | O |
| 608. | CN | 3 | 3 | O |
| 609. | CN | 4 | 3 | O |
| 610. | CN | 2 | 4 | O |
| 611. | CN | 3 | 4 | O |
| 612. | CN | 4 | 4 | O |
| 613. | F | 2 | 1 | O |
| 614. | F | 3 | 1 | O |
| 615. | F | 4 | 1 | O |
| 616. | F | 2 | 2 | O |
| 617. | F | 3 | 2 | O |
| 618. | F | 4 | 2 | O |
| 619. | F | 2 | 3 | O |
| 620. | F | 3 | 3 | O |
| 621. | F | 4 | 3 | O |
| 622. | F | 2 | 4 | O |
| 623. | F | 3 | 4 | O |
| 624. | F | 4 | 4 | O |
| 625. | Cl | 2 | 1 | O |
| 626. | Cl | 3 | 1 | O |
| 627. | Cl | 4 | 1 | O |
| 628. | Cl | 2 | 2 | O |
| 629. | Cl | 3 | 2 | O |
| 630. | Cl | 4 | 2 | O |
| 631. | Cl | 2 | 3 | O |
| 632. | Cl | 3 | 3 | O |
| 633. | Cl | 4 | 3 | O |
| 634. | Cl | 2 | 4 | O |
| 635. | Cl | 3 | 4 | O |
| 636. | Cl | 4 | 4 | O |
| 637. | OC$_2$H$_5$ | 2 | 1 | O |
| 638. | OC$_2$H$_5$ | 3 | 1 | O |
| 639. | OC$_2$H$_5$ | 4 | 1 | O |
| 640. | OC$_2$H$_5$ | 2 | 2 | O |
| 641. | OC$_2$H$_5$ | 3 | 2 | O |
| 642. | OC$_2$H$_5$ | 4 | 2 | O |
| 643. | OC$_2$H$_5$ | 2 | 3 | O |
| 644. | OC$_2$H$_5$ | 3 | 3 | O |
| 645. | OC$_2$H$_5$ | 4 | 3 | O |
| 646. | OC$_2$H$_5$ | 2 | 4 | O |
| 647. | OC$_2$H$_5$ | 3 | 4 | O |
| 648. | OC$_2$H$_5$ | 4 | 4 | O |
| 649. | OH | 2 | 1 | O |
| 650. | OH | 3 | 1 | O |
| 651. | OH | 4 | 1 | O |
| 652. | OH | 2 | 2 | O |
| 653. | OH | 3 | 2 | O |
| 654. | OH | 4 | 2 | O |
| 655. | OH | 2 | 3 | O |
| 656. | OH | 3 | 3 | O |
| 657. | OH | 4 | 3 | O |
| 658. | OH | 2 | 4 | O |
| 659. | OH | 3 | 4 | O |
| 660. | OH | 4 | 4 | O |
| 661. | OMe | 2 | 1 | O |
| 662. | OMe | 3 | 1 | O |
| 663. | OMe | 4 | 1 | O |

-continued

If1

| No. | R¹ | n | m | x |
|-----|-----|---|---|---|
| 664. | OMe | 2 | 2 | O |
| 665. | OMe | 3 | 2 | O |
| 666. | OMe | 4 | 2 | O |
| 667. | OMe | 2 | 3 | O |
| 668. | OMe | 3 | 3 | O |
| 669. | OMe | 4 | 3 | O |
| 670. | OMe | 2 | 4 | O |
| 671. | OMe | 3 | 4 | O |
| 672. | OMe | 4 | 4 | O |
| 673. | CN | 2 | 1 | O |
| 674. | CN | 3 | 1 | O |
| 675. | CN | 4 | 1 | O |
| 676. | CN | 2 | 2 | O |
| 677. | CN | 3 | 2 | O |
| 678. | CN | 4 | 2 | S |
| 679. | CN | 2 | 3 | S |
| 680. | CN | 3 | 3 | S |
| 681. | CN | 4 | 3 | S |
| 682. | CN | 2 | 4 | S |
| 683. | CN | 3 | 4 | S |
| 684. | CN | 4 | 4 | S |
| 685. | F | 2 | 1 | S |
| 686. | F | 3 | 1 | S |
| 687. | F | 4 | 1 | S |
| 688. | F | 2 | 2 | S |
| 689. | F | 3 | 2 | S |
| 690. | F | 4 | 2 | S |
| 691. | F | 2 | 3 | S |
| 692. | F | 3 | 3 | S |
| 693. | F | 4 | 3 | S |
| 694. | F | 2 | 4 | S |
| 695. | F | 3 | 4 | S |
| 696. | F | 4 | 4 | S |
| 697. | Cl | 2 | 1 | S |
| 698. | Cl | 3 | 1 | S |
| 699. | Cl | 4 | 1 | S |
| 700. | Cl | 2 | 2 | S |
| 701. | Cl | 3 | 2 | S |
| 702. | Cl | 4 | 2 | S |
| 703. | Cl | 2 | 3 | S |
| 704. | Cl | 3 | 3 | S |
| 705. | Cl | 4 | 3 | S |
| 706. | Cl | 2 | 4 | S |
| 707. | Cl | 3 | 4 | S |
| 708. | Cl | 4 | 4 | S |
| 709. | OC$_2$H$_5$ | 2 | 1 | S |
| 710. | OC$_2$H$_5$ | 3 | 1 | S |
| 711. | OC$_2$H$_5$ | 4 | 1 | S |
| 712. | OC$_2$H$_5$ | 2 | 2 | S |
| 713. | OC$_2$H$_5$ | 3 | 2 | S |
| 714. | OC$_2$H$_5$ | 4 | 2 | S |
| 715. | OC$_2$H$_5$ | 2 | 3 | S |
| 716. | OC$_2$H$_5$ | 3 | 3 | S |
| 717. | OC$_2$H$_5$ | 4 | 3 | S |
| 718. | OC$_2$H$_5$ | 2 | 4 | S |
| 719. | OC$_2$H$_5$ | 3 | 4 | S |
| 720. | OC$_2$H$_5$ | 4 | 4 | S |

EXAMPLE C

Ampoules for Injection

A solution of 100 g of a compound of the general formula I and 5 g of disodium hydrogenphosphate is adjusted to pH 6.5 using 2 N hydrochloric acid in 3 l of double-distilled water, sterile filtered and filled into injection ampoules, and lyophilized. Sterile conditions were adhered to here. Each injection ampoule contains 5 mg of the active component of the general formula I.

EXAMPLE D

A mixture of 20 g of a compound of the general formula I is mixed with 100 g of soya lecithin and 1400 g of cocoa butter with warming and poured into hollows. Each suppository contains 20 mg of the active component.

EXAMPLE E

A solution comprising 1 g of a compound of the general formula I, 9.38 g of $NaH_2PO_4 \times 2\ H_2O$, 28.48 g of $Na_2HPO_4 \times 12\ H_2O$ and 0.1 g of benzalkonium chloride is prepared using 940 ml of double-distilled water. The solution is adjusted to pH 6.8 and made up to one litre with double-distilled water and sterilized by irradiation. This solution can be used in the form of eye drops.

EXAMPLE F

Ointment 500 mg of a compound of the general formula I are blended with 99.5 g of raw petroleum jelly under aseptic conditions.

EXAMPLE G

Tablets 100 g of a compound of the general formula I, 1 kg of lactose, 600 g of microcrystalline cellulose, 600 g of corn-starch, 100 g of polyvinyl-pyrrolidone, 80 g of talc and 10 g of magnesium stearate are mixed and pressed in a customary manner to give tablets such that one tablet contains 100 mg of the active component.

EXAMPLE H

Coated Tablets

Tablets are prepared as in Example 7 and then coated in a known manner with sucrose, maize starch, talc, tragacanth gum and colorants.

EXAMPLE I

Capsules

Hard gelatin capsules are filled with a compound of the general formula I in a known manner such that each capsule contains 5 mg of the active component.

EXAMPLE J

Inhalation Spray 14 g of a compound of the general formula I are dissolved in 10 l of isotonic saline solution. The solution is filled into commercially obtainable spray containers which have a pump mechanism. The solution can be sprayed into the mouth or into the nose. One puff of spray (approximately 0.1 ml) corresponds to a dose of 0.14 mg of a compound of the general formula I.

The invention claimed is:

1. A Compound of formula I wherein $R^1$ is H, OH, OA, CN, Hal, COR or $CH_2R$,

R is OH, OA, $NH_2$, NHA or $NA_2$, $R^2$ and $R^3$ are H or A,

A is an alkyl group with 1-10 atoms,

X is O or S,

Hal is F, Cl, Br or I n is 2-6, m is 1-4 p is 0, 1, 2, 3 or 4 or a salt, enantiomer, racemate or mixture of enantiomers thereof.

2. A compound according to claim 1, wherein $R^1$ is F or CN.

3. A compound according to claim 1, wherein $R^3$ is H.

4. A compound according to claim 1 of the formula I1 to I5:

-continued
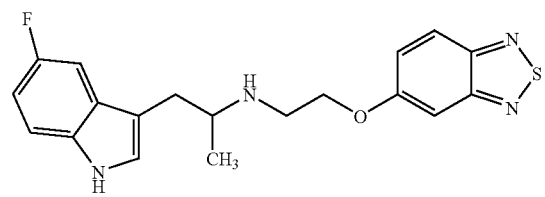
I3
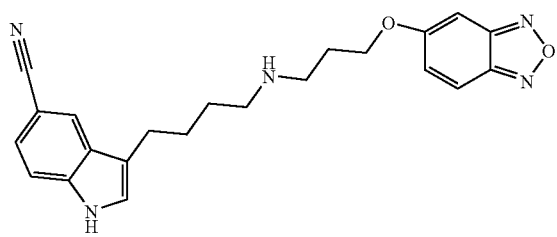
I4
or
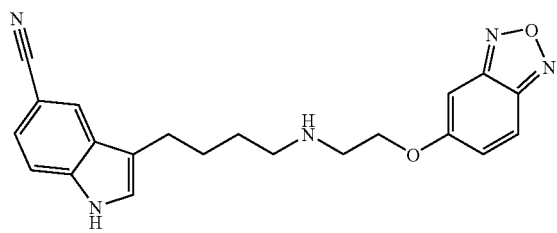
I5
or a salt, enantiomer or racemate thereof.
5. A pharmaceutical composition comprising a formula I according to Claim 1 or physiologically acceptable salt thereof and a pharmaceutically acceptable carrier.
* * * * *